United States Patent [19]

Smith et al.

[11] Patent Number: 5,361,757
[45] Date of Patent: Nov. 8, 1994

[54] SUBCUTANEOUS RADIATION REFLECTION PROBE

[75] Inventors: Roger E. Smith, Bountiful; Jon Neese, Salt Lake City, both of Utah

[73] Assignee: Utah Medical Products, Inc., Midvale, Utah

[21] Appl. No.: 18,936

[22] Filed: Feb. 17, 1993

[51] Int. Cl.$^5$ .............................................. A61B 5/00
[52] U.S. Cl. ................................... 128/633; 128/664; 128/665
[58] Field of Search ............... 128/632, 633, 634, 642, 128/664, 665, 670, 698; 667/92; 356/39–41

[56] References Cited

U.S. PATENT DOCUMENTS

| | | | |
|---|---|---|---|
| 4,658,825 | 4/1987 | Hochberg et al. | 128/634 |
| 4,926,867 | 5/1990 | Kanda et al. | 128/633 |
| 5,025,787 | 6/1991 | Sutherland et al. | 128/698 X |
| 5,069,213 | 12/1991 | Polczynski | 128/665 X |
| 5,099,842 | 3/1992 | Mannheimer et al. | 128/633 |
| 5,154,175 | 10/1992 | Gunther | 128/633 |

FOREIGN PATENT DOCUMENTS

9118549 12/1991 WIPO .............................. 128/642

*Primary Examiner*—Lee S. Cohen
*Assistant Examiner*—Samuel Gilbert
*Attorney, Agent, or Firm*—Thorpe North & Western

[57] ABSTRACT

A subcutaneous radiation reflection probe for measuring oxygen saturation in living tissue includes an elongate drive shaft on one end of which is detachably coupled a mounting cup. The mounting cup includes a hollow for receiving and holding a base element on which is mounted a spiral needle which coils outwardly from the mounting cup to terminate in a pointed end. A window is formed in the spiral needle near the pointed end thereof for receiving and holding a radiation emitter, such as a light emitting diode. A radiation detector is disposed on the base element within the coil of the spiral needle. The probe may be used to measure oxygen saturation in living tissue, such as a fetal scalp, by inserting the mounting cup and drive shaft through an introducer into a woman's vagina until the spiral needle contacts the fetal scalp. The drive shaft may then be rotated so that the spiral needle rotates into the scalp, after which energizing pulses are applied to the radiation emitter to cause it to emit radiation and illuminate the fetal scalp tissue into which the needle is inserted. The radiation detector detects a portion of this radiation, depending upon the oxygen saturation of the tissue, and develops a signal to thus provide a measure of the oxygen saturation.

51 Claims, 4 Drawing Sheets

SUBCUTANEOUS RADIATION REFLECTION PROBE

BACKGROUND OF THE INVENTION

This invention relates to a probe for measuring electromagnetic radiation from subcutaneously illuminated living tissue to thereby, for example, provide a measure of oxygen saturation of the tissue. Such a measure in a fetus can provide information as to the health and well-being of the fetus.

The problems encountered in childbirth can in many instances be avoided if the health condition of the fetus can be monitored on a continuous basis. If a change in the health condition is detected, the attending physicians can immediately take actions to correct the situation if possible. One such health condition of interest is the fetal oxygen supply which, of course, should be maintained at proper levels if the most problem free delivery is to be achieved.

A number of approaches have been devised for measuring oxygen supply in the fetus or, more particularly, measuring oxygen saturation in the tissue of the fetus. These approaches typically involve placing a probe of some type in contact with fetal skin and, in some cases, inserting some part of the probe into the skin. Some of these probes are fairly large and therefore cannot be inserted through the cervix into contact with the fetus until significant dilation has taken place. Of course, this would limit the effectiveness and utility of the probe since monitoring could only begin at some time after the delivery process had already begun.

Another approach to measuring oxygen saturation in fetal tissue involves so-called reflectance oximetry. In this approach, the probe is provided with a light source which directs light toward the tissue, and a light detector which detects light reflected from the tissue. The amount of light detected provides a measure of oxygen saturation of the tissue against which the probe is placed. A problem with this approach is that the signal level of detected reflected light is oftentimes poorly modulated, making accurate measurements difficult. This low modulation level in part is caused by scattering of light in the cutaneous layer so that much of the light reflected back to the detector is unmodulated light.

SUMMARY OF THE INVENTION

It is a general object of the invention to provide an efficient, easy to use subcutaneous radiation reflection probe.

It is a further object of the invention to provide such a probe which is especially suitable for measuring oxygen saturation in fetal tissue.

It is another object of the invention to provide such a probe which is highly accurate, reliable and repeatable.

It is an additional object of the invention to provide such a probe having a construction which allows effective illumination of tissue, and detection of such illumination, to thereby provide an accurate measure of oxygen saturation.

It is still another object of the invention to provide such a probe which may be used with little discomfort to the patient.

It is also an object of the invention to provide such a probe which may also be utilized to measure fetal heart rate.

It is also an object of the invention, in accordance with one aspect thereof, to provide an easy to use and effective connection/disconnection mechanism for attaching the probe to power supplies and monitoring equipment.

The above and other objects of the invention are realized in a specific illustrative embodiment of a subcutaneous reflection probe for measuring electromagnetic radiation from illuminated tissue. The probe includes a hollow needle preferably formed into a spiral and having a pointed free end for insertion into the tissue. A window is formed in a wall of the needle near the free end. The opposite end of the needle is attached to a base element. A radiation emitter is disposed in the hollow of the needle to selectively emit radiation through the window to thereby illuminate the tissue, and a radiation detector is disposed on the base element so as to face the tissue when the free end of the needle is inserted therein, for measuring the radiation from the illuminated tissue.

In accordance with one aspect of the invention, the window is positioned at a location in the needle so as not to face the radiation detector so that all light ultimately reaching the radiation detector is a result of reflectance rather than direct transmission from the emitter to the detector.

In accordance with another aspect of the invention, the radiation emitter includes a pair of side-by-side light-emitting diodes which alternatively emit radiation.

In accordance with still another aspect of the invention, the probe includes a drive shaft connectable to the base element to facilitate insertion of the base element into a patient's vagina and into contact with a fetus such that if more than a certain amount of force is applied to the drive shaft, the drive shaft will disconnect or slip from the base element to thereby limit the damage which might otherwise be caused to the fetus.

In an additional aspect of the invention, the needle is connected to serve as one electrode of a fetal heart rate measuring device, and another electrical conductor is provided on the base element to serve as the other electrode of the heart rate measuring device.

BRIEF DESCRIPTION OF THE DRAWINGS

The above and other objects, features and advantages of the invention will become apparent from a consideration from the following detailed description presented in connection with the accompanying drawings in which.

DETAILED DESCRIPTION

Figure 1:
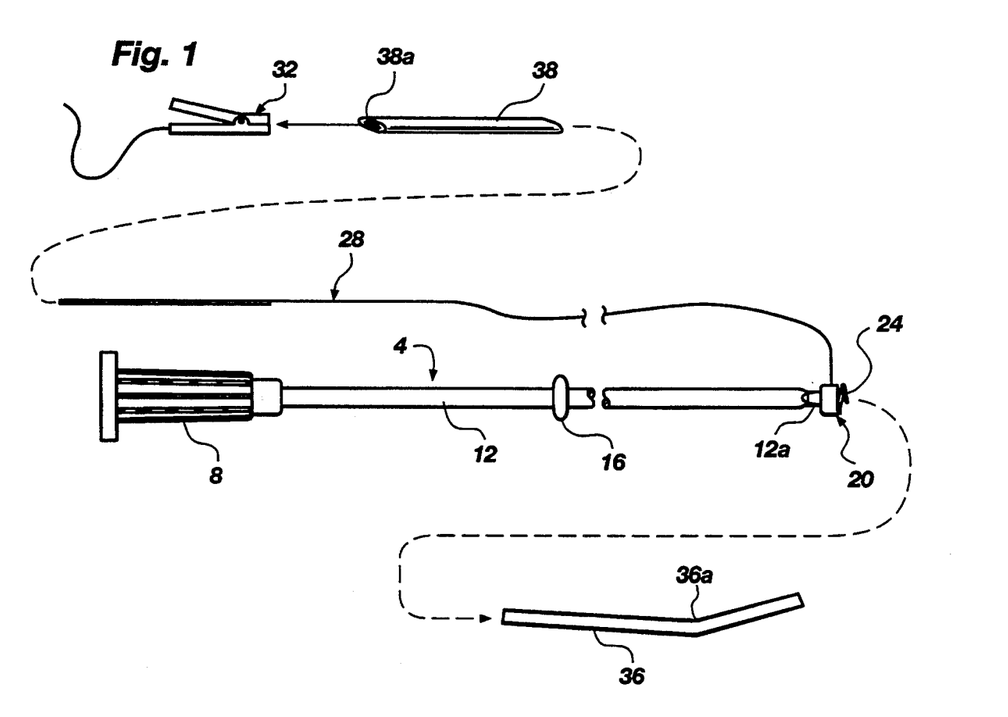
FIG. 1 is a side, elevational view of a fetal tissue oxygen probe or oximeter made in accordance with the principles of the present invention.

Referring to FIG. 1, the fetal tissue oxygen monitor is shown to include a drive shaft 4 having a handle 8 for grasping by a user, and a laterally flexible and substantially torsionally and longitudinally inflexible shaft 12. Advantageously, the shaft 12 is made of high density polyethylene material.

The shaft 12 includes an annular enlargement 16 formed at about the midpoint of the shaft for purposes to be described momentarily. The shaft 12 has a free end 12a which is formed to detachably couple to a mounting cup 20 in which is disposed a spiral needle 24 and circuitry (not shown) for monitoring oxygen saturation of fetal tissue in which the spiral needle is inserted. As discussed earlier, this monitoring or measuring is carried out indirectly by measuring electromagnetic radiation reflected from illuminated fetal tissue.

A flexible circuit carrier 28, having a generally flat profile, is coupled at one end to the circuitry held in the mounting cup 20 and is connectable at the other end to a clip connector 32 which, in turn, is connected to conventional power supply equipment and recording and display apparatus (not shown).

Also shown in FIG. 1 is a conventional so-called introducer, or guide tube 36. In use, the introducer 36, with drive shaft at least partially inserted therein, is inserted through the vagina until it reaches the fetal "presenting part" (typically the head of the fetus, but could be another body part), and then the drive shaft 4, with mounting cup 20 attached to the free end 12a thereof, is advanced through the introducer 36 until the spiral needle 24 reaches the "presenting part." The handle 8 of the drive shaft 4 is then rotated to cause the spiral needle 24 to rotate against the scalp of the fetus and thus rotate into the scalp in preparation for measuring the oxygen saturation in the scalp. The enlargement 16 formed on the shaft 12 serves as a bearing guide to center the shaft within the introducer 36, and reduce the clearance between the shaft 12 and inside wall of the introducer. This helps to keep the circuit carrier 28 from becoming jammed within the introducer during insertion. This insertion process will be further described later.

Also shown in FIG. 1 is a tubular member 38 having a central bore 38a which has a generally oval cross-section for receiving the flat circuit carrier 28. The tubular member 38 is provided to allow easy grasping by a user who can readily twist or rotate the tubular member to cause twisting or rotating of the circuit carrier 28 threaded therethrough. The tubular member 38 would be used in this manner to untwist the needle 24 and mounting cup 20 from the scalp of a fetus at a time when the drive shaft 4 has already been removed from the mounting cup. If the mounting cup 20 were easily graspable by a user, then a user could simply grasp it and untwist the needle 24 and mounting cup from the scalp—but the mounting cup is quite small and difficult to handle—therefore, provision of the tubular member 38 allows or facilitates untwisting and removal of the needle and mounting cup from the fetal scalp. The tubular member 38 would simply be slid up the circuit carrier 28 until it contacted the mounting cup 20 so that any twisting of the tubular member causes the circuit carrier, and thus mounting cup, to twist.

Figure 2:
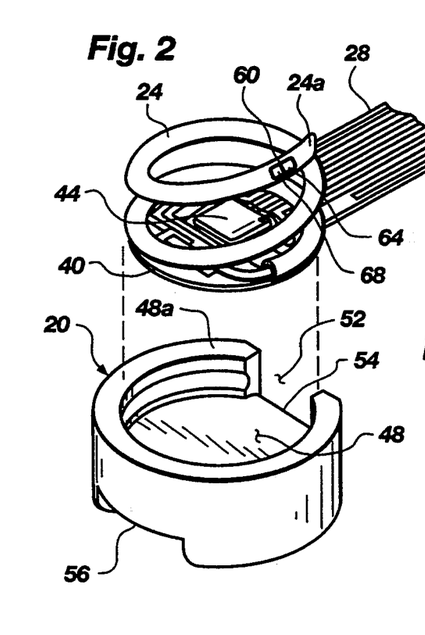
FIG. 2 is a perspective, partially fragmented view of a spiral needle and base element on which it is disposed, positioned above a mounting cup, all in accordance with the principles of the present invention.

FIG. 2 shows a portion of the circuit carrier 28 integrally formed with a base element 40 on which the spiral needle 24 is mounted. The spiral needle 24 spirals upwardly from the base element 40 about an imaginary axis which is generally perpendicular to the surface of the base element. The base element 40 includes a photodetector 44 mounted centrally on the base element to coincide generally with and intersect the axis of the spiral. Some additional circuit components are also mounted on the base element 40.

The base element 40, made of a flexible insulation material such as polyamide, is generally circular to fit snugly within a circular open hollow 48 formed in the top of mounting cup 20. An opening 52 is formed in side wall 48a which defines the hollow 48 to allow the circuit carrier 28 to exit from the hollow. The lower edge 54 of the opening 52 is rounded (also see FIG. 6B) to reduce the bending stress which might otherwise be applied to the carrier circuit 28.

When the base element 40 is placed in the hollow 48, the sidewall 48a of the hollow will at least partially surround the base element and the photodetector 44—since the mounting cup 20 is advantageously made of an opaque material (e.g., opaque polycarbonate plastic), the sidewall 48a will thus generally block ambient light from reaching the photodetector.

With the base element 40 placed in the hollow 48, the spiral needle 24 winds upwardly to extend out of the hollow. As seen in FIG. 2, the needle 24 is formed with just over two complete turns so that through the first turn, the spiral needle is still within the hollow 48, but begins to emerge from the hollow with the second turn.

In order to hold the base element 40 in place in the hollow 48, a translucent, electrically nonconductive potting material, such as an optical epoxy, is deposited over the base element and partly over the lower end of the spiral needle 24. The potting material is selected to be clear to allow light to pass therethrough to the photodiode 44 as will be discussed later. In addition to holding the base element 40 in place in the hollow 48, the potting material also serves to protect the photodiode 44 and other circuit components disposed on the base element from harmful environmental conditions during use.

The underside of the mounting cup 20 is formed with a slot 56 for receiving the free end 12a (FIG. 1) of the drive shaft 12. As will be further discussed later on, the structure of the slot 56 and free end 12a of the drive shaft allow for easy coupling of the drive shaft to the mounting cup 20, and decoupling therefrom when more than a predetermined amount of force (pulling) is applied to the drive shaft.

Figures 3, 3A:
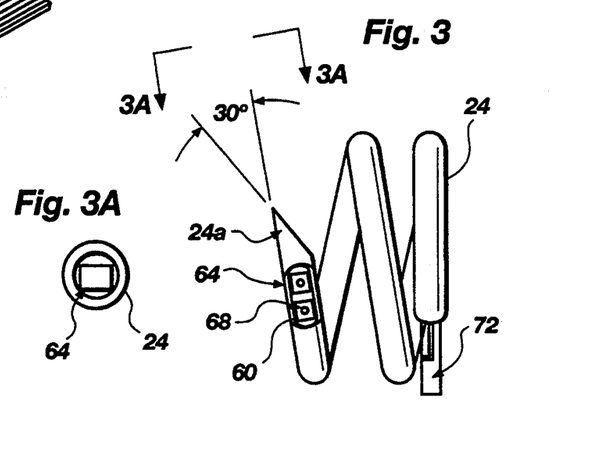
FIGS. 3 and 3A show respectively a side, elevational view of the spiral needle of FIG. 2, and an end view of the spiral needle taken along lines A—A of FIG. 3.

Referring now to FIGS. 3 and 3A, there is shown respectively a side, elevational view of the spiral needle 24, and an end view of the needle taken along lines A—A of FIG. 3. As seen in FIG. 3 (and also in FIG. 2), a window or opening 60 is formed in the spiral needle 24 on the outside convex curvature portion of the needle, near the pointed end 24a thereof. Thus, the window 60 faces radially outwardly from the imaginary axis about which the spiral needle 24 is coiled. Advantageously, the window 60 is located as close to the needle tip 24a as possible to minimize bending forces on the needle at the window location which necessarily results from insertion of the needle into tissue and subsequent movement of the tissue.

Another important feature of the location of the window 60 is that the window does not extend to the sharpened point 24a. Rather, a small arch of needle material remains between the window and the beveled point and this serves as a bonding location for potting material which will be placed in the hollow of the needle to hold light emitting elements in place (to be discussed later).

It might also be mentioned that the bevel point 24a of the needle is located forwardly of the needle to contact tissue first and assist in entry (rather than providing the bevel on the opposite side in which case the entire beveled portion of the needle might first contact the tissue rather than just the point first contacting the tissue). Advantageously, the spiral needle 24 is made of stainless steel hypodermic tubing.

As earlier indicated, disposed in the needle 24 at the window 60 is a pair of light emitting diodes (LEDs) 64 and 68 for selectively emitting or transmitting light from the needle through the window. The LEDs are mounted on a flexible insulator 72 such as polyamide (FIG. 4) which extends through the needle 24 so that the two LEDs are exposed through the window 60. The LEDs 64 and 68 are held in place by transparent, electrically nonconductive potting material. This potting material substantially fills the hollow of the needle 24 and the window 60 to hold the LEDs 64 and 68, and flexible insulator 72, firmly in place. Conductors 76, for example gold wire (FIG. 4), connect the LEDs 64 and 68 to conductor traces 88 disposed on the insulator 72, and these conductor traces are, in turn, connected to circuitry on the base element 40 which extend along the circuit carrier 28 to a signal source for energizing the LEDs. The LEDs 64 and 68 are held in place on the insulator 72 by conductive adhesive 84, and the conductors 76 are bonded to the LEDs 64 and 68 and to the conductor traces 88 by wire bonds 80. As already mentioned, a clear, insulative potting material is disposed over both LEDs 64 and 68 and the connecting conductors both to maintain electrical isolation between component parts which are not to be electrically connected, and to hold the LEDs in place in the hollow of the needle.

Figures 4, 5:
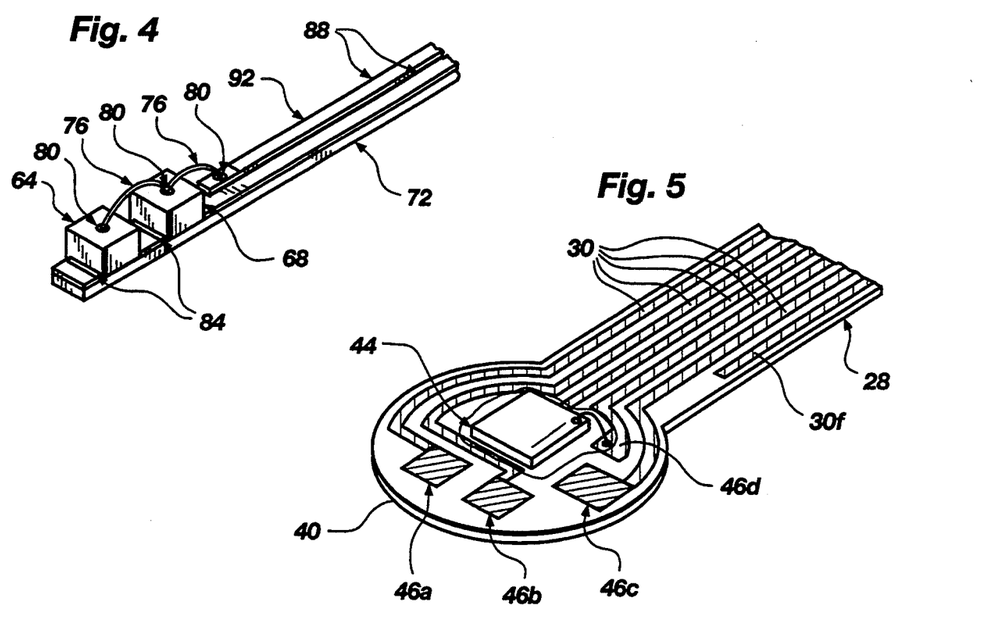
FIG. 4 is a perspective, partially fragmented view of the light emitting element which is disposed in the spiral needle of FIG. 3.
FIG. 5 is a perspective, partially fragmented view of the base element and flex circuit on which the spiral needle is mounted in accordance with the present invention.

The location of the window 60 and thus LEDs 64 and 68 near the point 24a of the needle, and on the outside or convex portion of the needle, serve to maximize the illuminated path length over which light emitted by the LEDs will have to travel in order to reach the photodetector 44. This is advantageous since the modulated (light) signal strength is roughly proportional to the illuminated tissue path length between the LEDs and the photodetector. Obviously, maximizing the modulated signal strength provides a more accurate reading of oxygen saturation in the tissue.

Advantageously, the LEDs 64 and 68 are selected to alternately emit light of different wavelengths. Thus, LED 64 might advantageously be a red LED and LED 68 might advantageously be an infrared LED, each of opposite polarity from the other. Thus, an AC driving signal supplied to conductors 76 will, during one half of the cycle, energize one of the LEDs and, during the other half cycle, energize the other LED. Because the LEDs are positioned in the tissue when measurements are made (since the spiral needle 24 is rotated into the tissue, for example, the fetal scalp), a much higher modulated light signal level is produced than if the light source were located outside of the tissue. One reason for this is that locating the photodetector outside of the tissue allows for a larger more sensitive light detector since the requirement for making it very small, for example, to fit within a needle, is not necessary.

Referring to FIG. 5, there is shown a perspective view of the base element 40 and a portion of the circuit carrier 28, unencumbered by the spiral needle. The circuit carrier 28 is shown to include six conductors 30 formed thereon, with four of the conductors being connected to electrical contact pads 46, and another conductor being coupled to the photodetector 44. The electrical contact pads 46a and 46b are for coupling to the LEDs 64 and 68 via conductive traces 88 (FIG. 4) to provide drive current; electrical contact pad 46d is for coupling to the photodetector 44 to carry detected light signals back to monitoring equipment. The photodetector 44 advantageously is a photodiode selected for high optical sensitivity at the two wavelengths of the LEDs 64 and 68.

Electrical contact pad 46c is provided for coupling to the spiral needle 24 to allow the spiral needle, along with conductor 30f (FIG. 5) to serve as electrodes suitable for monitoring fetal heart rate of a fetus in which the probe is inserted. Use of the pair of electrodes for monitoring fetal or human heart rates is well-known, but provision of the electrical contact pad 46c, coupled to the spiral needle, along with the electrical conductor 30f, when coupled to appropriate and conventional monitoring equipment, allows the oxygen probe of the present invention to also be used as a fetal heart rate device.

Figure 6:
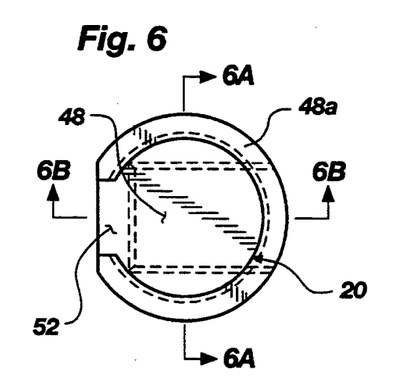
FIGS. 6, 6A and 6B show respectively a top plan view of the mounting cup of FIG. 2, a rear cross-sectional view of the mounting cup taken along lines A—A of FIG. 6, and a side, cross-sectional view of the mounting cup taken along lines B—B of FIG. 6.
Figure 6A:
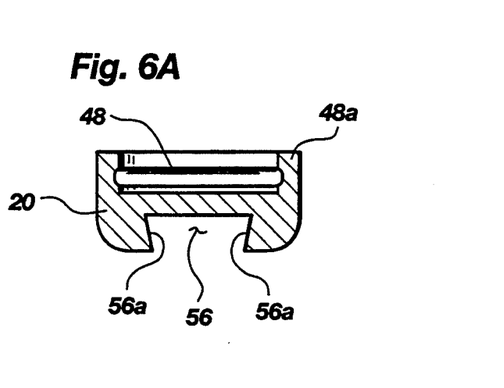
Figure 6B:
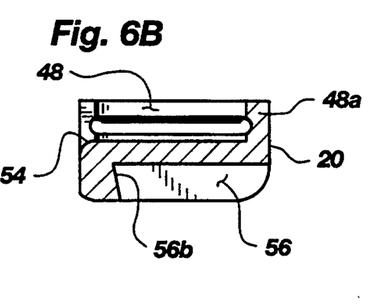

FIGS. 6, 6A and 6B show various views of the mounting cup 20 (also shown in FIG. 2). FIG. 6 is a top, plan view showing the sidewall 48a, with the opening 52 formed on one side thereof. FIG. 6A is a cross-sectional view of the mounting cup 20 taken along lines A—A of FIG. 6 and shows the hollow 48, sidewall 48a, and slot 56 formed on the underside. The sidewalls 56a of the slot 56, as shown in FIG. 6A, extend downwardly and slightly inwardly in a dovetail fashion. The slot 56 opens on the side opposite that in which the opening 52 is formed, as best seen in FIGS. 6 and 6B. FIG. 6B shows a side, elevational view of the mounting cup 20 taken along lines B—B of FIG. 6 and shows the slot 56 as having a back wall 56b which slopes downwardly and slightly inwardly similar to the sidewalls 56a best seen in FIG. 6A. The shape of the slot 56, including dovetailing sidewalls and back wall, allows for the easy insertion of the free end 12a of the drive shaft 4 into the slot, and then the rotation of the drive shaft to cause the mounting cup to rotate and thus the spiral needle to rotate into tissue against which it is placed. The configuration of the free end 12a of the drive shaft 4 (to be described later), along with use of suitably compliant material, allows for a release or pull away from the slot 56 when a certain force is applied to the drive shaft after the probe has been attached to fetal tissue. Also, the corners of the free end 12a of the drive shaft 4 are slightly rounded so that if a certain torque is applied to the drive shaft, and the rotation of the mounting cup 20 meets resistance, the drive shaft will slip within the slot 56. This reduces the chance of injury to the tissue which might otherwise result from twisting the drive shaft 4, mounting cup and spiral needle too hard. Also, once the spiral needle has been rotated into the tissue until the mounting cup 20 contacts the tissue (so no more rotation is possible), the drive shaft 4 will slip and this will be felt by a user to indicate no more rotation is necessary.

Figure 7:
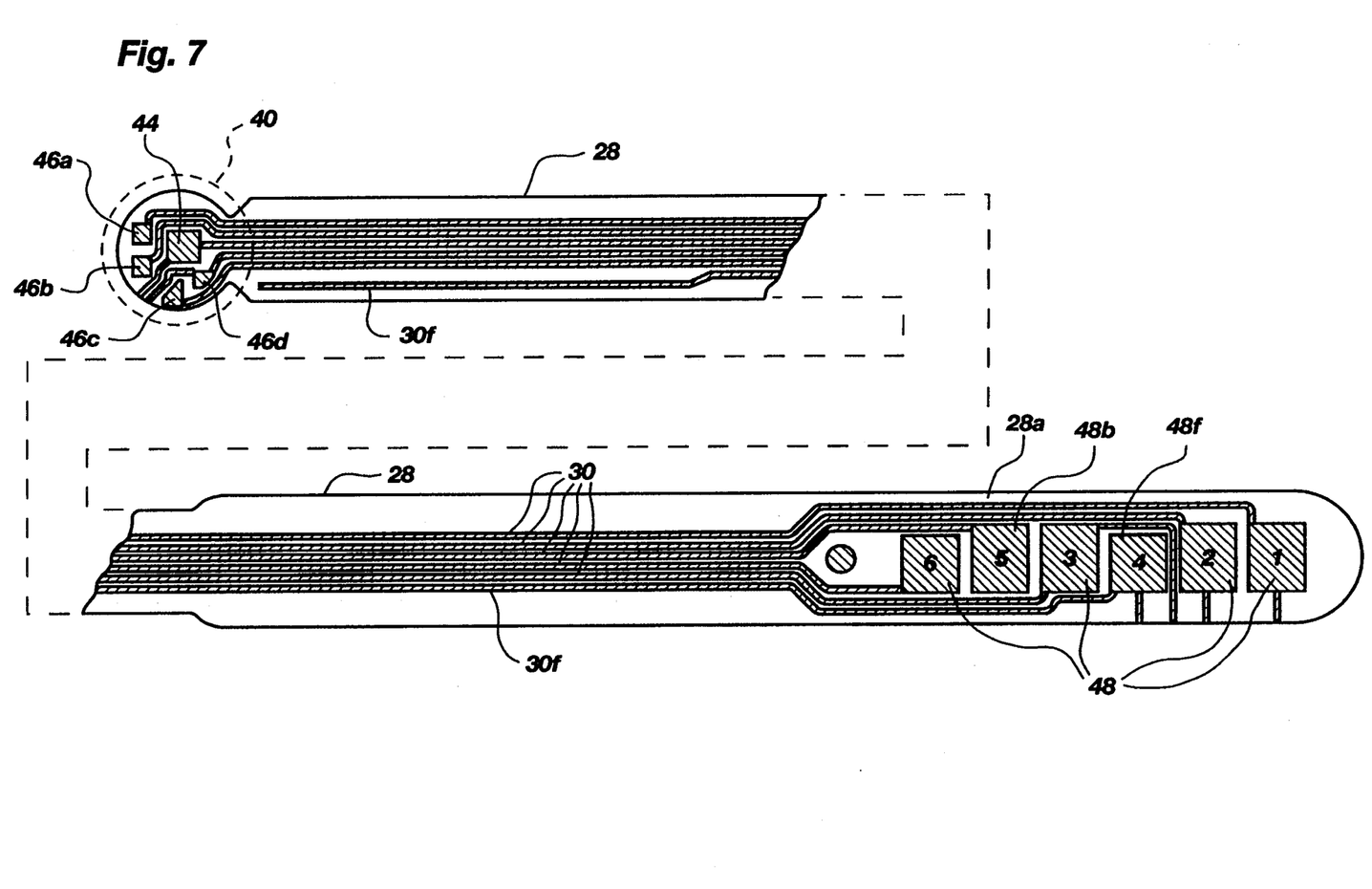
FIG. 7 is a fragmented top plan view of one embodiment of the flex circuit of the present invention.

FIG. 7 shows top plan views of fragmented portions of the circuit carrier 28, including the six conductor traces 30 extending in parallel with one another along the top of the circuit carrier to connect conductor pads 46 located on the base element 40 to corresponding conductor pads 48 located at a proximal end 28a of the circuit carrier 28. One of the conductor pads, 48f, is coupled to conductor 30f which serves as a reference electrode for fetal heart rate monitoring, as discussed earlier, and another of the conductor pads, 46b, is connected to the photodetector 44. Note that the conductor pads on the proximal end 28a are all located in sequence longitudinally on the circuit carrier 28; the reason for this is to facilitate easy connection of those pads to a clip connector shown in FIG. 9. The six conductors 30 are illustratively constructed of copper traces, while the conductor pads on both the base element 40 and proximal end 28a of the carrier circuit 28 are illustratively gold plated to provide corrosion resistance; the copper traces are covered with a flexible insulation material such as a polyester film.

Figure 8:
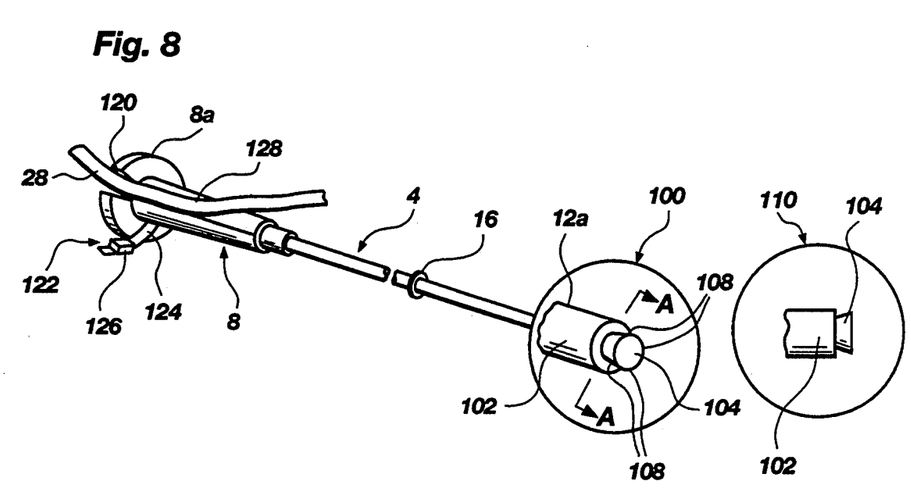
FIG. 8 is a fragmented perspective view of one embodiment of the drive shaft of the present invention.

FIG. 8 is a perspective, fragmented view of the drive shaft 4, showing the handle 8, enlargement 16, and free end 12a. The free end 12a is shown in enlarged views in both perspective view at 100 and side view at 110 (taken along lines A—A of view 100), to include a generally cylindrical terminal section 102, on the end of which is formed an attachment nipple 104. The attachment nipple 104 has a generally square cross-section, but including rounded corners 108, as discussed earlier. As best seen in the side view shown at 110, the attachment nipple 104 flares forwardly and outwardly from the cylindrical terminal section 102, in a dovetail configuration to snugly fit in the slot 56 of the mounting cup 20 (FIGS. 6, 6A and 6B.) With the dovetail slot 56 and dovetail attachment nipple 104 configuration, the attachment nipple may be readily slipped into the slot 56 and then rotated to cause the mounting cup 20 to rotate. But when a certain resistance is reached, for example, indicating that the spiral needle 24 has rotated all the way into the tissue, the attachment nipple 104 is caused to slip within the slot 56 so that the mounting cup and needle aren't forced to continue rotating and otherwise cause injury to tissue in which the needle is inserted. Also, the attachment nipple 104 will pull out of the slot 56 if more than a certain resistance is reached when pulling the drive shaft 4 away from the mounting cup 20.

The handle 8 of the drive shaft 4 includes an enlarged rear section 8a in which is formed a slot 120, the purpose of which is to receive and hold the circuit carrier 28. The slot 120 simply serves as a holder for temporarily receiving the carrier circuit 28 while using the probe to thereby keep the circuit carrier from getting entangled or otherwise in the way. To hold the circuit carrier 28 in the slot 120, a keeper 122 is molded integrally with the handle 8. The keeper 122 includes an integrally molded living hinge 124, and a snap in cover 126 which snaps into a slot 128 formed in the handle 8 into which the circuit carrier 28 is placed when the probe is to be placed in use. The slot 128 is just wide enough to snugly receive and hold the cover 126 which, in turn, holds the circuit carrier 28 in the slot 128.

Figure 9:
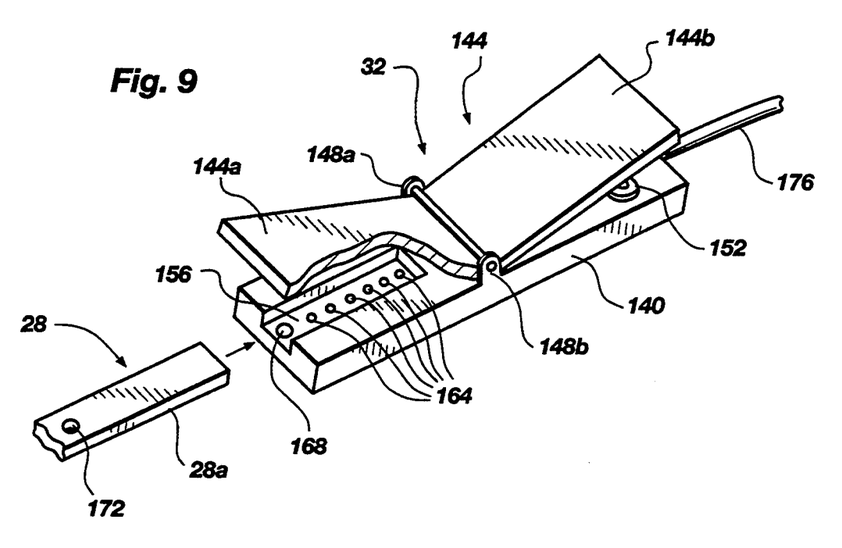
FIG. 9 is a fragmented perspective view of one embodiment of a flex circuit connector of the present invention.

FIG. 9 is a perspective, partially cutaway view of the clip connector 32 (FIG. 1) for connecting monitor and display equipment (not shown) to the circuit carrier 28 and ultimately to the LEDs, and photodetector. The clip connector 32 includes a base plate 140, on which is pivotally mounted an angled pivot plate 144. The pivot plate 144 includes a clamping section or finger 144a and a lever section or finger 144b which extends from one end of the clamping finger at an angle from the plane defined by the clamping finger, generally as indicated in FIG. 9. The pivot plate 144 is pivotally mounted between two ear pieces 148a and 148b which extend upwardly from the sides of the base plate 140, generally at the midpoint thereof. The pivot plate 144 is biased by a spring 152, located between the base plate 140 and pivot finger 144b, to urge the clamping finger 144a downwardly into contact with the base plate 140. Of course, pressing downwardly on the pivot finger 144b causes the clamping finger 144a to move upwardly away from the base plate 140.

An elongate channel 156 is formed in the top surface of the base plate 140 at one end thereof to extend generally under the clamping finger 144a.

Formed to protrude upwardly from the bottom wall of the channel 56 are a plurality of flexible spring-loaded electrical contact pins 164, formed in a row and spaced so as to contact corresponding conductor pads 48 (FIG. 7) formed on the proximal end 28a of the circuit carrier 28 (FIG. 1) when the proximal end is inserted into the channel 156. To ensure alignment of the conductor pads on the proximal end 128a with the electrical contacts 164, a guide nipple 168 is formed to extend upwardly from the bottom of the channel 156 to register and extend into a guide hole 172 formed in the proximal end 28a of the circuit carrier 28. In this way, the circuit carrier 28 can be easily placed in the channel 156 and properly aligned by simply first pressing downwardly on the pivot finger 144b, causing the clamping finger 144a to pivot upwardly from the base plate 140, and then placing the proximal end 28a in the channel 156 so that the guide nipple 168 extends through the guide hole 172; then, the pivot finger 144b may be released to allow the clamping finger 144a to pivot downwardly to contact the proximal end 28a and forces the conductor pads on the underneath surface thereof into electrical contact with the electrical contacts 164.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A subcutaneous reflection probe for measuring E/M radiation from illuminated tissue comprising
   a hollow needle having a pointed free end for insertion in the tissue and a base end, with a window formed in a wall of the needle, the window being positioned other than in the pointed free end,
   a radiation emitter means disposed in the hollow of the needle for selectively emitting radiation through the window to illuminate the tissue, the radiation emitter means comprising a radiation generating device positioned at the window,
   a base element on which the base end of the needle is secured, and
   a radiation detector means disposed on the base element so as to face the tissue when the free end of the needle is inserted therein, for measuring the radiation from the illuminated tissue, the window being positioned on the hollow needle so that the radiation detector means is substantially off any optical line-of-sight with the window and so that radiation emitted from the radiation emitter means is directed away from the radiation detector means such that radiation received by the radiation detector means is modulated by the tissue.

2. A probe as in claim 1 wherein the needle is formed into a spiral, and wherein the window is formed at a convex curvature portion of the needle.

3. A probe as in claim 2 wherein the needle is disposed so that its imaginary spiral axis intersects the radiation detector means.

4. A probe as in claim 2 further including a transparent potting material disposed in the window of the needle over the radiation emitter means to hold the radiation emitter means in place in the needle.

5. A probe as in claim 2 further including a receptacle open at top thereof, into which the base element is disposed so that the needle extends out the top of the receptacle.

6. A probe as in claim 5 further including a transparent potting material disposed in the receptacle over the base element and about a portion of the needle to hold the base element and needle in place in the receptacle.

7. A probe as in claim 6 wherein said needle spiral comprises two turns, a first one of which is disposed in the potting material and the second of which extends from the potting material, out the receptacle.

8. A probe as in claim 2 further including a base element mounting cup comprising a body having a receiving hollow formed at a top thereof receiving and holding the base element so that the needle extends upwardly and out of the receiving hollow, and having a slot formed on an underside thereof for receiving an end of a drive shaft so that the mounting cup is caused to rotate as the drive shaft is rotated, the mounting cup also having a rotational resistance which has a predetermined release level.

9. A probe as in claim 8 wherein the receiving hollow is formed with opaque sidewalls which at least partially surround and block ambient light from reaching the radiation detector means disposed on the base element.

10. A probe as in claim 9 wherein the sidewalls of the hollow include an opening to allow electrical conductors connected to the base element to exit from the hollow.

11. A probe as in claim 8 wherein the slot is formed to have a generally rectangular bottom-view cross-section with a back wall, an opening opposite the back wall, and spaced-apart parallel sidewalls which slope downwardly and inwardly towards one another in a dovetail fashion, said probe further including an elongate drive shaft, one end of which is formed to have a generally rectangular end-view cross-section just dimensionally smaller than the rectangular cross-section of the slot, with upwardly and outwardly flaring sidewalls fitting snugly in the slot when slid therein through the opening.

12. A probe as in claim 11 wherein the rectangular cross-section of the end of the drive shaft having a plurality corners, each of the corners being rounded to allow slipping of the drive shaft in the slot when the rotational resistance of the mounting cup exceeds a predetermined level.

13. A probe as in claim 11 wherein the sidewalls of said one end of the drive shaft, and the sidewalls of said slot are dimensioned to allow the one end of the drive shaft to be pulled downwardly and out of the slot when a certain force is applied to the drive shaft.

14. A probe as in claim 13 wherein the force required to pull the one end of the drive shaft from the slot is about one pound.

15. A probe as in claim 11 wherein said drive shaft is generally laterally flexible and longitudinally and torsionally inflexible.

16. A probe as in claim 1 wherein the radiation emitter means comprises first and second radiation emitters disposed side by side in the window of the needle for alternately emitting radiation.

17. A probe as in claim 16 wherein the radiation emitters comprise light-emitting diodes.

18. A probe as in claim 17 wherein one light-emitting diode is a red light emitter, and wherein the other light-emitting diode is an infrared light emitter.

19. A probe as in claim 17 wherein one light-emitting diode is of a first polarity, and wherein the other light-emitting diode is of a second polarity, opposite the first polarity, said radiation emitter means further comprising means for supplying alternating current to the two light-emitting diodes to cause the light-emitting diodes to alternately emit light.

20. A probe as in claim 19 wherein said radiation emitter means further includes a flexible, elongate insulator, wherein said alternating current supplying means includes a pair of conductors disposed in parallel on the insulator, and wherein the two light-emitting diodes are disposed in line with one another and with the two conductors on the insulator at one end thereof, and are coupled to the conductors.

21. A probe as in claim 20 wherein said radiation emitter means further includes an insulative coating disposed over the conductors, light-emitting diodes, and insulator.

22. A probe as in claim 1 further including
an elongate multiple-conductor flexible circuit, one end of which is coupled to the radiation emitter means for delivering electrical signals thereto, and to the radiation detector means for carrying signals therefrom, and
clip means for coupling electrically to the other end of the flexible circuit and to a plurality of conductors thereof.

23. A probe as in claim 22 wherein said clip means comprises
a base plate including a groove receiving said other end of the flexible circuit, and
an angled pivot finger pivotally joined to the base plate, said pivot finger having a first branch which is biased to lie flat over a portion of the base plate, and a second branch which extends at an angle upwardly from the first branch and which, when pressed downwardly, causes the first branch to pivot away from the base plate.

24. A probe as in claim 23 wherein said flexible circuit includes a multiplicity of electrical contact pads disposed at said other end and connected to respective conductors of the flexible circuit, and wherein said clip means further includes a multiplicity of electrical contact pins disposed in the groove of the base plate of the second finger to contact respective contact pads when said one end of the flexible circuit is placed in the groove, and the first branch is biased into contact with the base plate.

25. A probe as in claim 24 wherein the flexible circuit further includes an alignment hole therein, located at said other end, and wherein the clip means further includes an alignment pin in said groove for insertion into the alignment hole when said other end of the flexible circuit is placed in the groove of the base plate.

26. A probe as in claim 22 further including an elongate drive shaft, one end joining to the base element and the other end for gripping to enable manually pushing said one end and base element, with the flexible circuit, through a tubular guide, said drive shaft including an enlargement located between said one end and other end.

27. A probe as in claim 26 wherein said other end of the drive shaft includes a handle for gripping by a user, said handle including a retainer means for holding the flexible circuit at the other end thereof in a fixed position relative to the handle.

28. A probe as in claim 27 wherein said retainer means comprises a groove into which the flexible circuit may be inserted for retention, and a keeper means for releasably holding the flexible circuit in the groove.

29. A probe as in claim 22 wherein said flexible circuit further includes a reference electrode conductor, and a heart rate conductor coupled to the needle, and wherein said probe further includes an insulative covering disposed over the flexible circuit except for said reference electrode conductor.

30. A probe as in claim 29 wherein said flexible circuit comprises
   an elongate, generally flat insulator,
   a plurality of conductors disposed in parallel on the insulator, wherein said reference electrode conductor is disposed on the insulator generally in parallel with said plurality of conductors, and
   an insulative covering disposed over said plurality of conductors and the insulator, leaving said reference electrode conductor exposed.

31. A probe as in claim 30 wherein said reference electrode conductor comprises a gold-plated copper trace.

32. A probe as in claim 22 further including an elongate tubular member having a bore with a generally oval cross-section, and wherein said flexible circuit is generally flat and fitting snugly into the bore of the tubular member so that when the tubular member is rotated, the flexible circuit is caused to rotate.

33. A subcutaneous reflectance oximeter comprising
   an elongate shaft having a grasping end and a probe end,
   a base detachably mounted on the probe end of the shaft,
   a spiral needle mounted on the base to coil outwardly therefrom about an axis which is generally collinear with a long axis of the shaft, said needle terminating in a point and including an opening in a side formed away from the point,
   light emitting means disposed in the needle for selectively emitting light through the opening into tissue in which the needle is inserted, the light emitting means comprising a light generating device positioned at the opening, and
   light detecting means disposed on the base for detecting light reaching the detecting means from illuminated tissue, the opening being positioned on the spiral needle so that the light detecting means is substantially off any optical line-of-sight with the opening and so that light emitted from the light emitting means is directed away from the light detecting means such that light received by the light detecting means is modulated by the tissue.

34. An oximeter as in claim 33 wherein said opening in the needle is disposed on a convex portion of the needle to face radially outwardly from the needle axis, and wherein the detecting means is disposed on the base generally coincident with the needle axis to face outwardly in a direction in which the needle coils.

35. An oximeter as in claim 33 wherein the light emitting means comprises a pair of light-emitting elements for alternately emitting light, each of different wavelength.

36. A subcutaneous reflection probe for measuring E/M radiation from illuminated tissue comprising
   a hollow needle having a pointed free end for insertion in the tissue and a base end, with a window formed in a wall of the needle, the window being positioned other than in the pointed free end and wherein the needle is formed into a spiral, and wherein the window is formed at a convex curvature portion of the needle,
   a radiation emitter means disposed in the hollow of the needle for selectively emitting radiation through the window to illuminate the tissue,
   a base element on which the base end of the needle is secured,
   a base element mounting cup comprising a body having a receiving hollow formed at a top thereof receiving and holding the base element so that the needle extends upwardly and out of the receiving hollow, and having a slot formed on an underside thereof for receiving an end of a drive shaft so that the mounting cup is caused to rotate as the drive shaft is rotated, the mounting cup also having a rotational resistance which has a predetermined release level, and
   a radiation detector means disposed on the base element so as to face the tissue when the free end of the needle is inserted therein, for measuring the radiation from the illuminated tissue.

37. A probe as in claim 36 wherein the receiving hollow is formed with opaque sidewalls which at least partially surround and block ambient light from reaching the radiation detector means disposed on the base element.

38. A probe as in claim 37 wherein the sidewalls of the receiving hollow include an opening to allow electrical conductors connected to the base element to exit from the receiving hollow.

39. A probe as in claim 36 wherein the slot is formed to have a generally rectangular bottom-view cross-section with a back wall, an opening opposite the back wall, and spaced-apart parallel sidewalls which slope downwardly and inwardly towards one another in a dovetail fashion, said probe further including an elongate drive shaft, one end of which is formed to have a generally rectangular end-view cross-section just dimensionally smaller than the rectangular cross-section of the slot, with upwardly and outwardly flaring sidewalls fitting snugly in the slot when slid therein through the opening.

40. A probe as in claim 29 wherein the rectangular cross-section of the end of the drive shaft having a plurality corners, each of the corners being rounded to allow slipping of the drive shaft in the slot when the rotational resistance of the mounting cup exceeds a predetermined level.

41. A probe as in claim 39 wherein the sidewalls of said one end of the drive shaft, and the sidewalls of said slot are dimensioned to allow the one end of the drive shaft to be pulled downwardly and out of the slot when a certain force is applied to the drive shaft.

42. A probe as in claim 41 wherein the force required to pull the one end of the drive shaft from the slot is about one pound.

43. A probe as in claim 39 wherein said drive shaft is generally laterally flexible and longitudinally and torsionally inflexible.

44. A probe as in claim 39 wherein the window is positioned at a location in the needle so as not to face the radiation detector means.

45. A probe as in claim 36 wherein the window is positioned at a location in the needle so as not to face the radiation detector means.

46. A probe as in claim 36 wherein the needle is formed into a spiral, and wherein the window is formed at a convex curvature portion of the needle.

47. A subcutaneous reflection probe for measuring E/M radiation from illuminated tissue comprising a hollow needle having a pointed free end for insertion in the tissue and a base end, with a window formed in a wall of the needle, the window being other than in the pointed free end, a radiation emitter means disposed in the hollow of the needle for selectively emitting radiation through the window to illuminate the tissue, a base element on which the base end of the needle is secured, a radiation detector means disposed on the base element so as to face the tissue when the free end of the needle is inserted therein, for measuring the radiation from the illuminated tissue, an elongate multiple-conductor flexible circuit, one end of which is coupled to the radiation emitter means for delivering electrical signals thereto, and to the radiation detector means for carrying signals therefrom, clip means for coupling electrically to the other end of the flexible circuit and to a plurality of conductors thereof, and an elongate drive shaft, one end joined to the base element and the other end for gripping to enable manually pushing said one end and base element, with the flexible circuit, through a tubular guide, said drive shaft including an enlargement located between said one end and other end wherein said other end of the drive shaft includes a handle for gripping by a user, said handle including a retainer means for holding the flexible circuit at the other end thereof in a fixed position relative to the handle.

48. A probe as in claim 47 wherein the window is positioned at a location in the needle so as not to face the radiation detector means.

49. A probe as in claim 47 wherein the needle is formed into a spiral, and wherein the window is formed at a convex curvature portion of the needle.

50. A probe as in claim 49 wherein the window is positioned at a location in the needle so as not to face the radiation detector means.

51. A probe as in claim 47 wherein said retainer means comprises a groove into which the flexible circuit may be inserted for retention, and a keeper means for releasably holding the flexible circuit in the groove.

* * * * *

REEXAMINATION CERTIFICATE (4087th)

United States Patent
Smith et al.

[11] B1 5,361,757
[45] Certificate Issued May 23, 2000

[54] SUBCUTANEOUS RADIATION REFLECTION PROBE

[75] Inventors: Roger E. Smith, Bountiful; Jon Neese, Salt Lake City, both of Utah

[73] Assignee: Utah Medical Products, Inc., Midvale, Utah

Reexamination Request:
No. 90/004,992, May 26, 1998

Reexamination Certificate for:
Patent No.: 5,361,757
Issued: Nov. 8, 1994
Appl. No.: 08/018,936
Filed: Feb. 17, 1993

[51] Int. Cl.$^7$ .................................................. A61B 5/00
[52] U.S. Cl. .......................... 600/310; 600/473; 600/476

[56] References Cited

U.S. PATENT DOCUMENTS

| | | |
|---|---|---|
| 3,167,658 | 1/1965 | Richter . |
| 3,224,433 | 12/1965 | Von Dalebor . |
| 3,599,629 | 8/1971 | Gordy . |
| 3,750,650 | 8/1973 | Ruttgers . |
| 4,321,931 | 3/1982 | Hon . |
| 4,776,340 | 10/1988 | Moran et al. ............................ 600/327 |
| 4,913,151 | 4/1990 | Harui et al. . |
| 5,069,213 | 12/1991 | Polzynski ................................ 600/323 |
| 5,551,424 | 9/1996 | Morrison et al. ....................... 600/338 |
| 5,662,103 | 9/1997 | Smith . |
| 5,733,305 | 3/1998 | Fleischmann . |

FOREIGN PATENT DOCUMENTS

| | | |
|---|---|---|
| 0 094 749 | 11/1983 | European Pat. Off. . |
| 0 135840 A2 | 4/1985 | European Pat. Off. . |
| 0 072 185 | 2/1986 | European Pat. Off. . |
| 0 247 777 A1 | 12/1987 | European Pat. Off. . |
| WO 89/09016 | 2/1989 | European Pat. Off. . |
| 0 104 619 B1 | 9/1991 | European Pat. Off. . |
| 0 285 307 B1 | 3/1995 | European Pat. Off. . |
| 0 454 886 B1 | 12/1995 | European Pat. Off. . |
| 38 10 008 C1 | 10/1989 | Germany . |
| 2155618 | 9/1985 | United Kingdom . |
| WO 88/02616 | 4/1988 | WIPO . |
| WO 90/01293 | 2/1990 | WIPO . |
| WO 90/04352 | 5/1990 | WIPO . |

OTHER PUBLICATIONS

M. Firbank, M. Hiraoka, M. Essenpreis and D.T. Delpy; Measurement of the Optical Properties of the Skull in the Wavelength Range 650–950 nm; Phys. Med. biol. 38, (1993) 503–510; printed in the UK.

*Primary Examiner*—Ruth S. Smith

[57] ABSTRACT

A subcutaneous radiation reflection probe for measuring oxygen saturation in living tissue includes an elongate drive shaft on one end of which is detachably coupled a mounting cup. The mounting cup includes a hollow for receiving and holding a base element on which is mounted a spiral needle which coils outwardly from the mounting cup to terminate in a pointed end. A window is formed in the spiral needle near the pointed end thereof for receiving and holding a radiation emitter, such as a light emitting diode. A radiation detector is disposed on the base element within the coil of the spiral needle. The probe may be used to measure oxygen saturation in living tissue, such as a fetal scalp, by inserting the mounting cup and drive shaft through an introducer into a woman's vagina until the spiral needle contacts the fetal scalp. The drive shaft may then be rotated so that the spiral needle rotates into the scalp, after which energizing pulses are applied to the radiation emitter to cause it to emit radiation and illuminate the fetal scalp tissue into which the needle is inserted. The radiation detector detects a portion of this radiation, depending upon the oxygen saturation of the tissue, and develops a signal to thus provide a measure of the oxygen saturation.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 8 is cancelled.

Claims 1, 9, 11, 33, 36, 47 are determined to be patentable as amended.

Claims 2–7, 10, 12–32, 34, 35, 37–46, 48–51, dependent on an amended claim, are determined to be patentable.

1. A subcutaneous reflection probe for measuring E/M radiation from illuminated tissue comprising
   a hollow needle having a pointed free end for insertion in the tissue and a base end, with a window formed in a wall of the needle, the window being positioned other than in the pointed free end,
   a radiation emitter means disposed in the hollow of the needle for selectively emitting radiation through the window to illuminate the tissue, the radiation emitter means comprising a radiation generating device positioned at the window,
   a base element on which the base end of the needle is secured, [and]
   a radiation detector means disposed on the base element so as to face the tissue when the free end of the needle is inserted therein, for measuring the radiation from the illuminated tissue, the window being positioned on the hollow needle so that the radiation detector means is substantially off any optical line-of-sight with the window and so that radiation emitted from the radiation emitter means is directed away from the radiation detector means such that radiation received by the radiation detector means is modulated by the tissue, *and*
   *a base element mounting cup comprising a body having a receiving hollow formed at a top thereof receiving and holding the base element so that the needle extends upwardly and out of the receiving hollow, and having a slot formed on an underside thereof for receiving an end of a drive shaft so that the mounting cup is caused to rotate as the drive shaft is rotated, the mounting cup also having a rotational resistance which has a predetermined release level.*

9. A probe as in claim [8] *1* wherein the receiving hollow is formed with opaque sidewalls which at least partially surround and block ambient light from reaching the radiation detector means disposed on the base element.

11. A probe as in claim [8] *1* wherein the slot is formed to have a generally rectangular bottom-view cross-section with a back wall, an opening opposite the back wall, and spaced-apart parallel sidewalls which slope downwardly and inwardly towards one another in a dovetail fashion, said probe further including an elongate drive shaft, one end of which is formed to have a generally rectangular end-view cross-section just dimensionally smaller than the rectangular cross-section of the slot, with upwardly and outwardly flaring sidewalls fitting snugly in the slot when slid therein through the opening.

33. A subcutaneous reflectance oximeter comprising
   an elongate shaft having a grasping end and a probe end,
   a base *element* detachably mounted on the probe end of the shaft, *the base element including a mounting cup comprising a body having a receiving hollow formed at a top thereof receiving and holding the base element so that a spiral needle extends upwardly and out of the receiving hollow, and having a slot formed on an underside thereof for receiving an end of a drive shaft so that the mounting cup is caused to rotate as the drive shaft is rotated, the mounting cup also having a rotational resistance which has a predetermined release level,*
   [a] *the* spiral needle mounted on the base *element* to coil outwardly therefrom about an axis which is generally collinear with a long axis of the shaft, said needle terminating in a point and including an opening in a side formed away from the point,
   light emitting means disposed in the needle for selectively emitting light through the opening into tissue in which the needle is inserted, the light emitting means comprising a light generating device positioned at the opening, and
   light detecting means disposed on the base for detecting light reaching the detecting means from illuminated tissue, the opening being positioned on the spiral needle so that the light detecting means is substantially off any optical line-of-sight with the opening and so that light emitted from the light emitting means is directed away from the light detecting means such that light received by the light detecting means is modulated by the tissue.

36. A subcutaneous reflection probe for measuring E/M radiation from illuminated tissue comprising
   a hollow needle having a pointed free end for insertion in the tissue and a base end, with a window formed in a wall of the needle, the window being positioned other than in the pointed free end and wherein the needle is formed into a spiral, and wherein the window is formed at a convex curvature portion of the needle,
   a radiation emitter means disposed in the hollow of the needle for selectively emitting radiation through the window to illuminate the tissue,
   a base element on which the base end of the needle is secured,
   a base element mounting cup comprising a body having a receiving hollow formed at a top thereof receiving and holding the base element so that the needle extends upwardly and out of the receiving hollow, and having a slot formed on an underside thereof for receiving an end of a drive shaft so that the mounting cup is caused to rotate as the drive shaft is rotated, the mounting cup also having a rotational resistance which has a predetermined release level, *wherein the receiving hollow is formed with opaque sidewalls which at least partially surround and block ambient light from reaching the radiation detector means disposed on the base element,* and
   a radiation detector means disposed on the base element so as to face the tissue when the free end of the needle is inserted therein, for measuring the radiation from the illuminated tissue.

47. A subcutaneous reflection probe for measuring E/M radiation from illuminated tissue comprising a hollow needle having a pointed free end for insertion in the tissue and a base end, with a window formed in a wall of the needle, the window being other than in the pointed free end, a radiation emitter means disposed in the hollow of the needle for selectively emitting radiation through the window to illuminate the tissue, a base element on which the base end of the needle is secured, a radiation detector means disposed on the base element so as to face the tissue when the free end of the needle is inserted therein, for measuring the radiation from the illumianted tissue, an elongate multiple-conductor flexible circuit, one end of which is coupled to the radiation emitter means for delivering electrical signals thereto, and to the radiation detector means for carrying signals therefrom, clip means for coupling electrically to the other end of the flexible circuit and to a plurality of conductors thereof, and an elongate drive shaft, one end joined to the base element and the other end for gripping to enable manually pushing said one end and base element, with the flexible circuit, through a tubular guide, said drive shaft including an enlargement located between said one end and other end wherein said other end of the drive shaft includes a handle for gripping by a user, said handle including a retainer means for holding the flexible circuit at the other end thereof in a fixed position relative to the handle, and

*a base element mounting cup comprising a body having a receiving hollow formed at a top thereof receiving and holding the base element so that the needle extends upwardly and out of the receiving hollow, and having a slot formed on an underside thereof for receiving an end of a drive shaft so that the mounting cup is caused to rotate as the drive shaft is rotated, the mounting cup also having a rotational resistance which has a predetermined release level.*

\* \* \* \* \*